United States Patent [19]

Perrin et al.

[11] 4,171,955
[45] Oct. 23, 1979

[54] PROCESS FOR IMPROVING THE COLOR YIELD AND FASTNESS PROPERTIES OF DYEINGS PRODUCED WITH ANIONIC DYES ON CELLULOSE FIBRE MATERIAL AND FLUORINE-CONTAINING CATIONIC COMPOUNDS

[75] Inventors: Pierre Perrin, Basel; Gert Hegar, Schönenbuch; Gérald Siegrist; Herbert Seiler, both of Riehen; Ulrich Horn, Basel, all of Switzerland

[73] Assignee: Ciba-Geigy Corporation, Ardsley, N.Y.

[21] Appl. No.: 805,069

[22] Filed: Jun. 9, 1977

[30] Foreign Application Priority Data

Jun. 16, 1976 [CH] Switzerland ............ 7674/76

[51] Int. Cl.$^2$ ............ C09B 65/00; D06P 3/60; D06P 5/02; C07D 239/22
[52] U.S. Cl. ............ 8/31; 8/29; 8/54.2; 8/21 C; 8/84; 8/74; 544/208; 544/326
[58] Field of Search ............ 8/84, 1 D, 1 S, 74, 8/31, 29, 54.2, 21 C; 260/256.4 N, 256.4 R; 544/208

[56] References Cited

U.S. PATENT DOCUMENTS

| | | | |
|---|---|---|---|
| 2,415,554 | 2/1947 | Friedheim | 544/208 |
| 3,122,542 | 2/1964 | Knusli et al. | 544/208 |
| 3,271,147 | 9/1966 | Bush | 8/84 |
| 3,310,557 | 3/1967 | Kleeman | 8/74 |
| 3,632,294 | 1/1972 | Hoelzle et al. | 8/1 D |
| 3,679,348 | 7/1972 | Asashi et al. | 8/1 D |

FOREIGN PATENT DOCUMENTS

| | | | |
|---|---|---|---|
| 633691 | 8/1936 | Fed. Rep. of Germany . | |
| 1094699 | 7/1957 | Fed. Rep. of Germany . | |
| 1134964 | 3/1960 | Fed. Rep. of Germany | 8/74 |
| 4514152 | 4/1967 | Japan | 8/74 |

OTHER PUBLICATIONS

Lutzel, G., Jour. Soc. of Dyers & Colorists, vol. 82, No. 8, 1966, pp. 293-299.
McCleary, H. R., et al., American Dyestuff Reporter, Jan. 16, 1967, pp. 28-39.

*Primary Examiner*—Melvyn I. Marquis

*Assistant Examiner*—Maria S. Tungol
*Attorney, Agent, or Firm*—Edward McC. Roberts

[57] ABSTRACT

A process for improving the color yield and the wet-fastness properties of dyeings produced on cellulose fibrous material with anionic dyes which process comprises treating the cellulose material before, during or after dyeing, with a fluorine-containing cationic compound of the formula

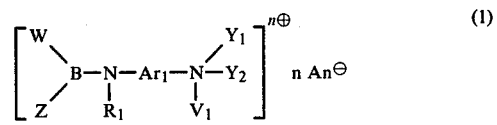

wherein
B represents a triazine or pyrimidine radical,
W represents a reactive fluorine atom,
Z represents halogen, lower alkyl, phenyl, lower alkoxy, lower alkylthio, phenoxy, phenylthio, —NH$_2$, or the group of the formula

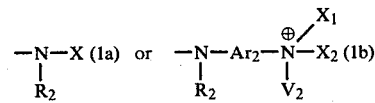

each of
Ar$_1$ and Ar$_2$ independently represents an aromatic radical,
each of
R$_1$ and R$_2$ independently represents hydrogen, lower alkyl or hydroxy-lower alkyl,
each of
X, X$_1$, X$_2$, Y$_1$, Y$_2$, V$_1$ and V$_2$ independently represents lower alkyl, benzyl, or lower alkyl which is substituted by halogen, hydroxyl or cyano, and X also represents phenyl or methylphenyl, or
each of the pair of substituents
X$_1$ and X$_2$ and Y$_1$ and Y$_2$, together with the nitrogen atom to which it is attached, represents a 5- or 6-membered heterocyclic radical,
An$^\ominus$ represents the anion of an organic or inorganic acid, and
n is 1 or 2.

14 Claims, No Drawings

PROCESS FOR IMPROVING THE COLOR YIELD AND FASTNESS PROPERTIES OF DYEINGS PRODUCED WITH ANIONIC DYES ON CELLULOSE FIBRE MATERIAL AND FLUORINE-CONTAINING CATIONIC COMPOUNDS

The present invention relates to a process for improving the colour yield and fastness properties of dyeings produced with anionic dyes on cellulose fibre material, to the liquors used for carrying out this process, which liquors contain the fluorine-containing, cationic, fibre-reactive compounds as fixing agent, to the fibrous material treated in accordance with this process, and also to the novel fluorine-containing compounds themselves and to a process for their manufacture.

It is known to dye cellulose material with anionic substantive or reactive dyes from aqueous medium without the addition of fixing agents. However, in many cases the colour yield of the dyeings and, in particular when substantive dyes are used, the wetfastness properties, are unsatisfactory. Although there are fixing agents by means of which these drawbacks can be diminished, the results nonetheless still leave something to be desired.

It is known, for example, that polyalkylenepolyamines can be used as fixing agents for substantive or reactive dyes. However, these compounds result in a marked impairment of the lightfastness. The proposal has furthermore been made to use fixing agents containing an epoxy group for improving the wetfastness properties of dyeings produced with substantive dyes on cellulose material. However, these fixing agents react sluggishly, so that the fixation has to be carried out under fairly drastic conditions, for example at elevated temperature or high pH values or with a lengthy reaction time. Moreover, these fixing agents have too little substantivity to be able to be used in the exhaustion process.

The present invention provides fluorine-containing cationic compounds which can be used as fixing agents for anionic dyes and, which surprisingly, effect a marked improvement in the colour yield both of dyeings on cellulose material with reactive and substantive dyes, while in addition the wetfastness properties, especially with substantive dyes, are substantially improved and the lightfastness is not impaired. These compounds are not only fibre-reactive but also substantive, so that they can be used in the exhaustion process.

On account of their pronounced reactivity, the compounds of the present invention can be applied under particularly mild conditions, so that the process can be carried out often at lower temperatures and/or lower pH values or also with shorter reaction times than when using the fixing agents referred to above which contain an epoxy group as reactive radical.

Accordingly, the present invention provides a process for improving the colour yield and the wetfastness properties of dyeings produced with anionic dyes on cellulose fibre material which comprises treating the cellulose material before, during or after the dyeing, with a fluorine-containing cationic compound of the formula

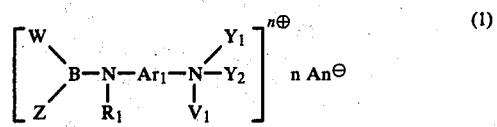

wherein
B represents a triazine or pyrimidine radical,
W represents a reactive fluorine atom,
Z represents halogen, lower alkyl, phenyl, lower alkoxy, lower alkylthio, phenoxy, phenylthio, —NH$_2$, or the group of the formula

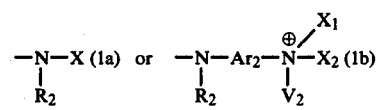

each of
Ar$_1$ and Ar$_2$ independently represents an aromatic radical, each of
R$_1$ and R$_2$ independently represents hydrogen, lower alkyl or hydroxy-lower alkyl,
each of
X, X$_1$, X$_2$, Y$_1$, Y$_2$, V$_1$ and V$_2$ independently represents lower alkyl, benzyl or lower alkyl which is substituted by halogen, hydroxyl or cyano, and X also represents phenyl or methylphenyl, or
each of the pair of substituents
X$_1$ and X$_2$ and Y$_1$ and Y$_2$, together with the nitrogen atom to which it is attached, represents a 5- or 6-membered, preferably saturated, heterocyclic radical,
An$^\ominus$ represents the anion of an organic or inorganic acid, and
n is 1 or 2.

In the definition of the radicals of fluorine-containing compounds, lower alkyl and lower alkoxy as a rule denote those groups or group components which contain 1 to 4, especially 1 to 3, carbon atoms, for example methyl, ethyl, n-propyl, isopropyl, or n-butyl, and methoxy, ethoxy or isopropoxy. Halogen in connection with all substituents referred to throughout this specification denotes, for example, bromine or preferably chlorine or fluorine.

In formula (1), B represents preferably the 1,3,5-triazine radical. As pyrimidine radical, B advantageously contains a further halogen atom. Examples of pyrimidine radicals represented by B are unsubstituted pyrimidinyl or 5-chloropyrimidyl.

Z represents in particular the group of the formula (1b). A halogen atom Z can be in particular a chlorine or, in particular, fluorine atom. Lower alkoxy represented by Z is preferably methoxy, ethoxy or isopropoxy and lower alkylthio represented by Z is preferably methylthio or ethylthio.

Ar$_1$ and Ar$_2$ represent preferably diphenylene or, in particular, phenylene, which can be substituted by halogen or lower alkyl. Preferably Ar$_1$ and Ar$_2$ represent phenylene.

A lower alkyl radical represented by R$_1$ and R$_2$ is in particular methyl or ethyl. A hydroxy lower alkyl represented by R$_1$ and R$_2$ is in particular 2-hydroxyethyl and 3-hydroxypropyl. Preferably, however, R$_1$ and R$_2$ represents hydrogen.

The radicals Y and X can be different from each other or they are preferably identical. $V_1$ and $V_2$ are also preferably the same.

Lower alkyl radicals represented by X, Y and V are in particular methyl or ethyl radicals. Substituted lower alkyl radicals X, Y and V are in particular haloalkyl, cyanoalkyl and hydroxyalkyl, each containing 2 to 4 carbon atoms, for example 2-chloroethyl, 2-cyanoethyl, 2-hydroxyethyl and 3-hydroxypropyl. Preferred radicals X, Y and V are methyl and ethyl. The radical X of the formula (1a) can also preferably represent phenyl or methylphenyl and the radicals V can also preferably be benzyl.

A heterocyclic radical represented by each of the pair of substituents $Y_1$ and $Y_2$ and $X_1$ and $X_2$ together with the nitrogen atom to which it is attached is, for example, a pyrrolidino, piperidino, pipecolino or morpholino radical.

Possible anions $An\ominus$ are both anions of inorganic acids, for example the chloride, bromide, fluoride, sulphate or phosphate ion and of organic acids, for example of aromatic or aliphatic sulphonic acids, such as the benzenesulphonate, p-toluenesulphonate, methanesulphonate or ethanesulphonate ion, and also the anions of acid alkyl esters of inorganic acids, such as the methosulphate and ethosulphate ion.

Important fluorine-containing compounds of the formula (1) are those of the general formula

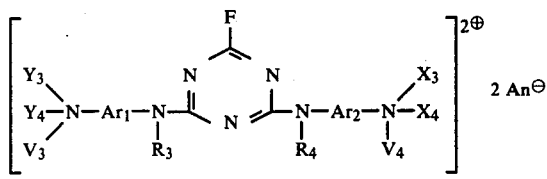

(2)

wherein
$Ar_1$ and $Ar_2$ have the given meanings and preferably represent phenylene,
each of
$R_3$ and $R_4$ independently represents hydrogen, methyl or ethyl, each of
$X_3$, $X_4$, $Y_3$ and $Y_4$ represents lower alkyl,
each of
$V_3$ and $V_4$ represents lower alkyl or benzyl, and
$An\ominus$ has the given meaning.

Particularly interesting fluorine-containing triazine compounds are those of the formula

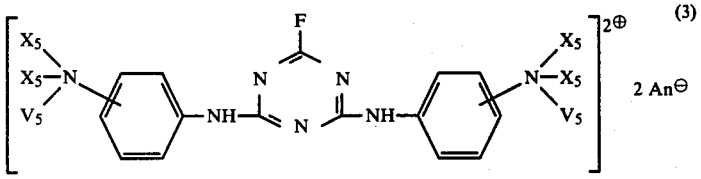

(3)

wherein
$X_5$ represents methyl or ethyl,
$V_5$ represents methyl, ethyl or benzyl, and
$An\ominus$ has the given meaning.

Suitable fluorine-containing pyrimidine compounds are also those of the formula (4)

wherein $X_5$, $V_5$ and $An\ominus$ are as defined hereinbefore, and T represents hydrogen or chlorine.

The cationic compounds of the general formula (1) are manufactured in a manner known per se, for example by reacting a compound of the formula $$W \atop Z \!\!\!\searrow\!\! B\text{-Hal}$$

(5)

wherein B, W and X have the given meanings and Hal represents halogen, with a quaternary ammonium salt of the formula $$\left[ HN-Ar_1-N{\atop R_1}{Y_1 \atop V_1}{Y_2} \right]^{\oplus} \quad An\ominus$$

(6)

wherein $R_1$, $Ar_1$, $Y_1$, $Y_2$, $V_1$ and $An\ominus$ have the given meanings.

The reaction conditions for the manufacture of the compounds of the formula (1) are to be so chosen that no premature exchange of mobile substituents takes place either as a consequence of too high a pH value of the reaction medium or of too high a temperature. The process is therefore carried out preferably in a strongly dilute aqueous medium under as mild temperature and pH conditions as possible, advantageously at temperatures between 0° and 50° C. and pH values between 6 and 8, preferably in the presence of agents which neutralise mineral acid, for example sodium carbonate or sodium hydroxide.

The treatment of the cellulose material with the fluorine-containing cationic compound of the formula (1) is effected preferably before or, in particular, after the dyeing of the fibrous material. If the treatment is carried out during the dyeing, then the cellulose material is preferably treated in two steps, whereby the dye and the cationic fixing agent of the formula (1) are advantageously applied by the slop-padding method in separate baths in order to avoid dye precipitations. The dye and the fixing agent are then fixed simultaneously by steaming for 30 seconds to 10 minutes, for example at 100°–105° C. By dyeings are also meant in this connection prints obtained by any methods using anionic dyes and in which the application of the compound of the formula (1) is preferably effected as an aftertreatment.

The pre- or aftertreatment with the fluorine-containing reactive compounds of the formula (1) can be carried out by means of the known padding methods suitable for the application of reactive dyes, for examples by the thermofixing, singly bath steaming, pad-jig, pad-dry, pad-roll or pad-steam method, with or without first drying the goods, or in particular by the cold pad-batch process. Preferably it is carried out by the exhaustion process, for example at a temperature between 10° and 100° C., preferably at room temperature (18°–25° C.). The liquor ratio can be chosen within a wide range, for example from 1:4 to 1:100, preferably 1:10 to 1:50.

The treatment liquors contain the compound of the formula (1) preferably in an amount between 0.1 and 20% by weight, in particular between 0.5 and 10% by weight, referred to the weight of the cellulose material, or in padding liquors, of 1 to 100 g/l, preferably 10 to 50 g/l, of padding liquor, whilst the squeezing effect in the padding process is advantageously 60 to 90% by weight.

In addition to the fluorine-containing reactive compound of the formula (1), these liquors also contain alkali, for example sodium carbonate, sodium bicarbonate, sodium hydroxide or alkali donors, for example sodium trichloroacetate, and also, if appropriate, further additives, such as urea, thickeners, for example alginates, salts, for example sodium chloride, or wetting agents.

The pretreatment with the compounds of the formula (1) can advantageously be combined with other pretreatment operations. For example, the reactive fixing agent of the formula (1) can be added to the alkaline bath in which raw cotton is customarily boiled before dyeing in order to remove impurities and thus the purification and pretreatment with the fixing agent can be carried out in one step.

Likewise it is possible to combine the aftertreatment with the compounds of the formula (1) with the customary after-treatment of the dyeings. It is known in the art that dyeings with reactive dyes, especially those with highly substantive dyes, must be rinsed and soaped very thoroughly to obtain good wetfastness properties. The aftertreatment operations can be substantially reduced by addition of the compounds of the formula (1) to the soaping bath.

Suitable cellulose material is that from natural and regenerated cellulose, for example hemp, linen, jute, viscose rayon, viscose staple fibre, and in particular cotton and also fibre blends, for example those of polyester/cotton, in which the polyester portion is optionally dyed before or afterwards.

The material to be dyed can be in any desired states of processing, for example as loose material (flocks), as doubled, prestretched staple fibre ribbon or in the form of filaments, yarns, wovens or knits.

By reactive dyes are meant the conventional anionic dyes which form a chemical bond with cellulose, for example the "Reactive Dyes" listed in the Colour Index, 3rd Edition (1971), Vol. 3, on pp. 3391–3562.

Suitable substantive dyes are the conventional anionic direct dyes, for example the "Direct Dyes" listed in the above Colour Index, Vol. 2, on pp. 2005–2478.

The present invention also relates to the aqueous liquors used for carrying out the process described herein. These liquors contain a compound of the formula (1) and optionally alkali or alkali donors and the further additives mentioned above.

In the following illustrative, but non-limitative, Examples, the percentages are by weight unless otherwise stated. The amounts of dye refer to commercially available, i.e. extended, products, and of fixing agents to pure substance. The Colour Index numbers refer to the 3rd Edition of the Colour Index.

EXAMPLE 1

1 g of a reactive fixing agent of the formula

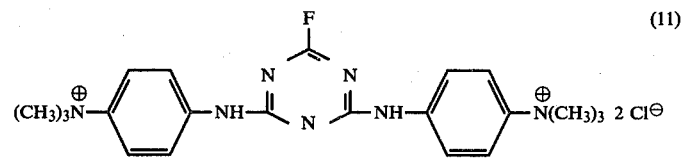

(11)

is dissolved in 200 ml of softened water of 25° C. To this solution is added 0.4 ml of 30% sodium hydroxide solution. 10 g of mercerised cotton yarn are then put into this liquor at 20°–25° C. and treated at this temperature for 30 minutes with constant agitation of the material. The bath is then emptied and the treated yarn is rinsed and subsequently dyed as follows:

0.3 g of a blue direct dye C.I. 24 401 is dissolved in 200 ml of softened water. Then 10 g of the above pretreated yarn are put into this solution at 50° C. and the bath is heated to boiling temperature in the course of 30 minutes while constantly agitating the substrate. After 15 minutes, 1 g of sodium chloride is added and dyeing is continued for 60 minutes at boiling temperature. The dyed material is subsequently rinsed with cold water and soaped for 5 minutes at boiling temperature to give a blue yarn which, in comparison with yarn which has been dyed by exactly the same method and pretreated as described above, but with a liquor which contains equal amounts of 2-epoxypropyl-trimethylammonium chloride or N-(2-epoxypropyl)-N-methyl-morpholinium chloride, is dyed two to three times more deeply.

EXAMPLE 2

0.2 g of a reactive fixing agent of the formula (11) is dissolved in 200 ml of softened water. To this solution is added 0.4 ml of 30% sodium hydroxide solution.

10 g of cotton yarn are put into this liquor at 20° C. and treated at this temperature for 30 minutes while constantly agitating the material. The bath is then emptied and the pretreated yarn is then dyed directly, without first being rinsed, as follows:

0.3 g of a dye of the formula

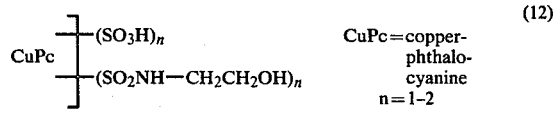

(12)

is dissolved in softened water. The yarn is put at 50° C. into this solution, which is heated to boiling temperature in the course of 30 minutes while constantly agitating the substrate. After 15 minutes, 1 g of sodium chloride is added and dyeing is continued for 30 minutes at boiling temperature. The material is then rinsed with water.

The yarn is dyed turquoise blue and, in comparison with yarn which has not been pretreated and has been dyed in exactly the same way, has a substantially deeper shade of good wet- and lightfastness properties.

EXAMPLE 3

10 g of cotton are pretreated as described in Example 2. The pretreated yarn is dyed as follows after first being rinsed:

0.3 g of a dye of the formula

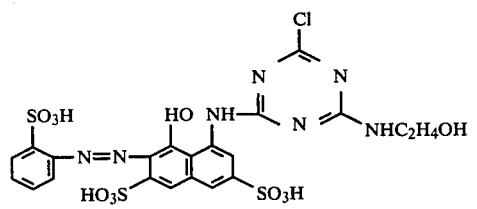

(13)

is dissolved in 200 ml of water, a solution of 18 g of sodium chloride in 100 ml of water is added and the pretreated yarn is put into this bath at 80° C. Dyeing is performed at this temperature for 30 minutes while constantly agitating the substrate and then 1.5 g of sodium carbonate and 0.6 ml of 30% sodium hydroxide solution are added. The fixation of the exhausted dye is effected over the course of 45 minutes at 80° C. The yarn is then rinsed cold, soaped at boiling temperature, and finally rinsed warm.

The yarn is dyed brilliant red and, in comparison with yarn which has not been pretreated and has been dyed by exactly the same method, has a substantially deeper shade of good wet- and lightfastness properties.

EXAMPLE 4

10 g of a cotton fabric which has been dyed or printed in the conventional way with a direct dye C.I. 24 401 are treated for 20 minutes at 20° C. in 250 ml of an aqueous liquor which contains 0.2 g of a fixing agent of the formula (11) and 0.5 ml of 30% sodium hydroxide solution. The fabric is subsequently rinsed cold, soaped twice for 10 minutes at the boil, rinsed once more and then dried. The cotton is dyed a deep blue shade of very good wetfastness, in particular of good fastness to washing at the boil.

The bulk of the dye becomes detached from the fabric when soaped at the boil and a very much paler dyeing is obtained by using the compound described in Example 1 of DAS No. 1,094,699 instead of the fixing agent of the formula (11).

EXAMPLE 5

10 g of a cotton fabric which has been dyed or printed in the conventional manner with the dye of the formula

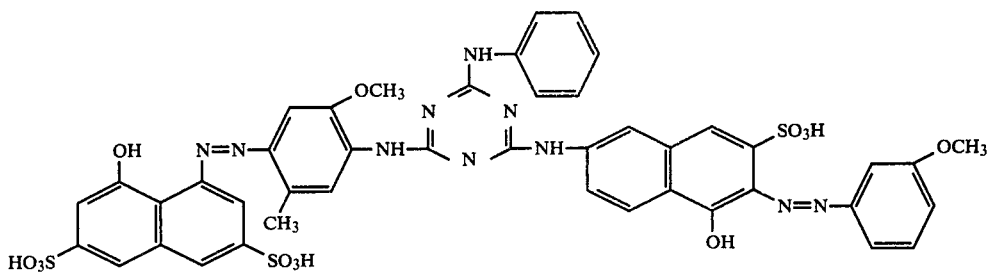

(14)

are treated for 20 minutes at 20° C. in 250 ml of an aqueous liquor which contains 0.2 g of a fixing agent of the formula (11) and 0.5 ml of 30% sodium hydroxide. The farbric is then rinsed cold, soaped at the boil twice for 10 minutes, rinsed again and then dried. The fabric is dyed a deep scarlet shade of very good wetfastness, in particular of good fastness to washing at the boil.

The bulk of the dye becomes detached from the fabric when soaped at the boil and a very much paler dyeing is obtained by using the compound described in Example 2, lines 87–95, of German Pat. No. 633,691, instead of the fixing agent of the formula (11).

EXAMPLE 6

10 g of a cotton fabric which has been dyed or printed in the conventional manner with the dye C.I. 28 160 in reference type strength is slop-padded on a padder to a liquor pick-up of 75% by weight with an aqueous liquor which contains, per liter, 30 g of a fixing agent of the formula (11) and 15 ml of 30% sodium hydroxide solution. The fabric is then rolled up, wrapped in a plastic sheet and stored at room temperature for 6 hours. The pretreated fabric is then rinsed cold, soaped at the boil, rinsed again and dried. The cotton fabric is dyed a deep red shade of very good wetfastness properties. The bulk of the dye becomes detached when fabric which has not been subjected to an aftertreatment with fixing agent is soaped at the boil. The wetfastness properties of such fabric are also substantially poorer.

EXAMPLE 7

Good results are also obtained by carrying out the procedure of Example 4, but using twice the amount of a fixing agent of the formula

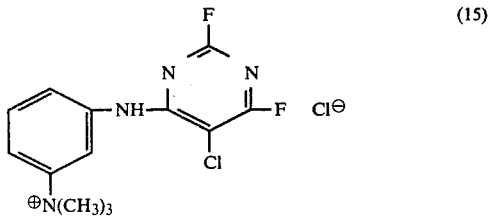

(15)

instead of the fixing agent of the formula (11), and effecting treatment for 40 minutes at 60° C.

EXAMPLE 8

10 g of cotton yarn are dyed in a long liquor (1:20) by the exhaustion process in conventional manner with a reactive dye of the formula

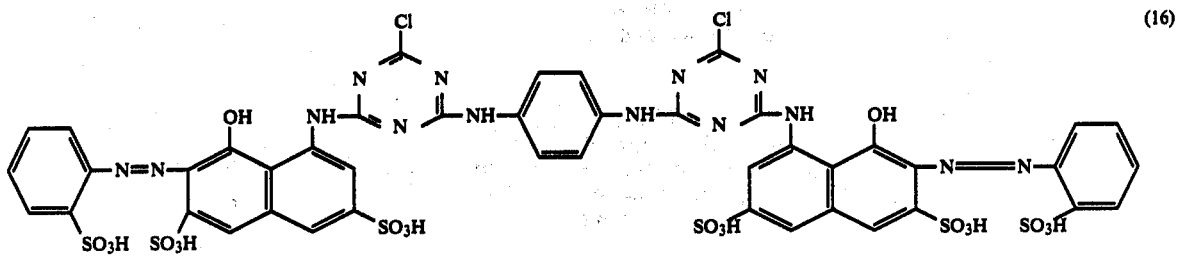

and rinsed cold for 5 minutes in 300 ml of water. Thereafter the dyed yarn is introduced cold into 300 ml of an aqueous liquor which contains, per liter, 3 g of a fixing agent of the formula (11), 5 g of sodium carbonate and 2 g of a non-ionogenic detergent. The liquor is heated to boiling temperature while constantly agitating the material. The goods are then rinsed hot for 5 minutes.

The cotton is dyed a deep red and has improved wetfastness properties compared with a fabric which has been dyed in the same way but has been finished in the soaping bath without the addition of the fixing agent.

EXAMPLE 9

A blended fabric consisting of 67% by weight of polyester and 33% by weight of cotton is slop-padded on a two-roll padder with a liquor which contains, per liter, 3.6 g of a disperse dye of the formula

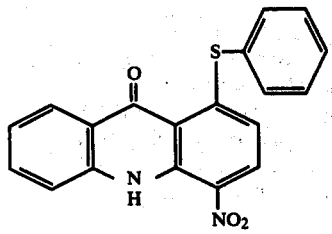

(17)

0.66 g of a direct dye C.I. 29 025

2 g of sodium alginate, and 0.5 ml of 80% acetic acid, squeezed out to a liquor pick-up of 75% by weight, dried at 100° C., and thermofixed for 60 seconds at 210° C.

Thereafter the fabric is slop-padded with a liquor which contains, per liter, 40 g of a fixing agent of the formula (11) and 15 ml of 30% sodium hydroxide solution and steamed for 60 seconds with saturated steam of 100°–102° C. The fabric is then rinsed continuously cold and at the boil. A golden yellow fabric with very good wetfastness properties, especially good washfastness at 60° C., is obtained.

Instead of by steaming, the fixation of the direct dye can also be accomplished by rolling up the fabric padded with the fixing agent and wrapping it in a plastic sheet and storing it for 6 hours at room temperature.

The fabric is subsequently washed off as described above.

EXAMPLE 10

The fixing agent of the formula (11) can be prepared

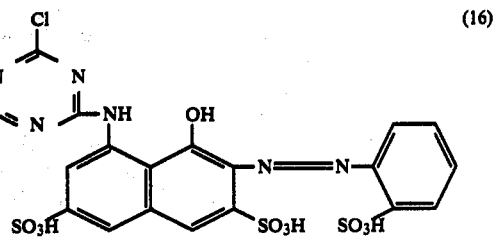

(16)

as follows: 3.4 g of cyanuric fluoride are added dropwise at 5° C. in the course of 2 hours to a solution of 9.3 g of trimethyl-(4-aminophenyl)-ammonium chloride in 50 ml of water while keeping the pH of the reaction mixture at 7 by the addition of a 30% sodium hydroxide solution. The reaction mixture is thereafter stirred for 8 hours and then diluted with 1 000 ml of acetone, whereupon a precipitate is obtained. This precipitate is isolated by filtration and extracted with 500 ml of methanol. The methanol is removed by distillation in vacuo, affording 5.8 g of the compound of the formula (11).

Further cationic compounds of the formula

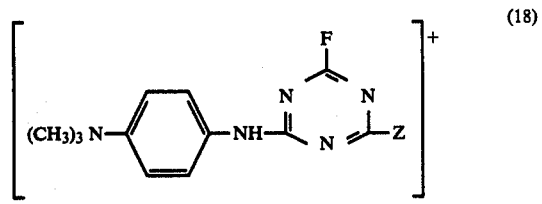

(18)

with similar application properties are obtained by reacting the acylating agents listed in the following table with trimethyl-(4-aminophenyl)-ammonium chloride in the molar ratio 1:1 in accordance with the particular of this Example.

TABLE

| Example | Acylating agent | Z | An$^\ominus$ |
|---|---|---|---|
| 11 | 2-methoxy-4,6-difluoro-1,3,5-triazine | —OCH$_3$ | F$^\ominus$ |
| 12 | 2-phenylamino-4,6-difluoro-1,3,5-triazine | —NH—C$_6$H$_5$ | Cl$^\ominus$ |
| 13 | 2-(2'-methylphenylamino)-4,6-difluoro-1,3,5-triazine | —NH—C$_6$H$_4$—CH$_3$ | Cl$^\ominus$ |
| 14 | 2-(N-ethyl-N-phenylamino)-4,6-difluoro-1,3,5-triazine | —N(C$_2$H$_5$)—C$_6$H$_5$ | Cl$^\ominus$ |
| 15 | 2-ethylthio-4,6-difluoro-1,3,5-triazine | —S—C$_2$H$_5$ | F$^\ominus$ |

EXAMPLE 16

The fixing agent of the formula (15) can be prepared as follows:

186.5 g of trimethyl-(3-aminophenyl)-ammonium chloride are dissolved in 1 000 g of water a pH 7. To this solution are added dropwise 168.5 g of 5-chloro-2,4,6- trifluoro-pyrimidine in the course of 40 minutes while keeping the pH of the reaction mixture between 6 and 7 by the addition of 2 N sodium hydroxide solution and keeping the temperature at 20° C. by the addition of ice. When no more starting material can be detected and the pH of the solution remains constant at 7, sodium chloride is added, whereupon the fixing agent of the formula (15) precipitates in crystalline form. The product melts at 230° C. with decomposition.

What we claim is:

1. A process for improving the colour yield and the wetfastness properties of dyeings produced on cellulose fiber material with anionic dyes which process comprises treating the cellulose material before, during or after dyeing, with a fluorine-containing cationic compound of the formula

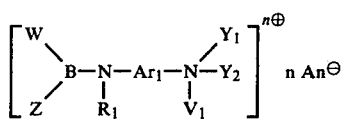

wherein

B represents a triazinyl or pyrimidyl radical,

W represents a reactive fluorine atom,

Z represents halogen, lower alkyl, phenyl, lower alkoxy, lower alkylthio, phenoxy, phenylthio, —NH$_2$, or the group of the formula

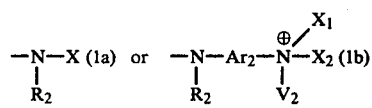

each of

Ar$_1$ and Ar$_2$ independently represents an aromatic radical, each of

R$_1$ and R$_2$ independently represents hydrogen, lower alkyl or hydroxy-lower alkyl, each of X, X$_1$, X$_2$, Y$_1$, Y$_2$, V$_1$ and V$_2$ independently represents lower alkyl, benzyl, or lower alkyl which is substituted by halogen, hydroxyl or cyano, and X also represents phenyl or methylphenyl, or each of the pair of substituents X$_1$ and X$_2$ and Y$_1$ and Y$_2$, together with the nitrogen atom to which it is attached, represents a 5- or 6-membered heterocyclic radical, An$^\ominus$ represents the anion of an organic or inorganic acid, and n is 1 or 2.

2. A process according to claim 1 which comprises the use of a compound of the formula (1), wherein B represents a 1,3,5-triazinyl radical.

3. A process according to claim 1, which comprises the use of a compound of the formula (1), wherein Z represents a group of the formula (1b).

4. A process according to claim 1 which comprises the use of a compound of the formula (1), wherein each of Ar$_1$ and Ar$_2$ represents phenylene.

5. A process according to claim 1 which comprises the use of a fluorine-containing compound of the formula

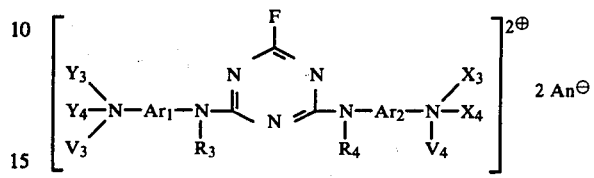

wherein

An$^\ominus$, Ar$_1$ and Ar$_2$ are as defined in claim 1, each of R$_3$ and R$_4$ independently represents hydrogen, methyl or ethyl, each of X$_3$, X$_4$, Y$_3$ and Y$_4$ represents lower alkyl, and each of V$_3$ and V$_4$ represents lower alkyl or benzyl.

6. A process according to claim 5 which comprises the use of a compound of the formula (2), wherein each of Ar$_1$ and Ar$_2$ represents phenylene.

7. A process according to claim 1 which comprises the use of a fluorine-containing triazinyl compound of the formula

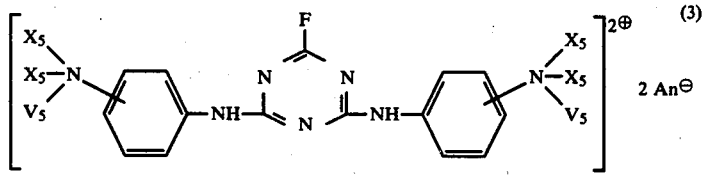

wherein

X$_5$ represents methyl or ethyl,

V$_5$ represents methyl, ethyl or benzyl, and

An$^\ominus$ is as defined in claim 1.

8. A process according to claim 7 which comprises the use of a fluorine-containing triazinyl-containing compound of the formula (3), in which each of X$_5$ and V$_5$ represents methyl and An$^\ominus$ represents a chloride ion.

9. A process according to claim 1 which comprises the use of a fluorine-containing pyrimidyl compound of the formula

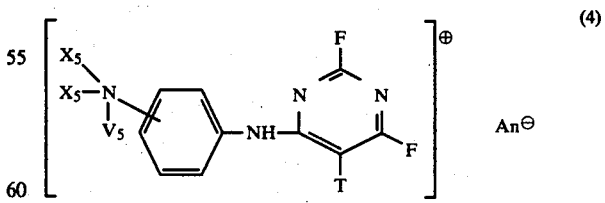

wherein

X$_5$ represents methyl or ethyl,

V$_5$ represents methyl, ethyl or benzyl,

T represents hydrogen or chlorine, and

An$^\ominus$ is as defined in claim 1.

10. A process according to claim 9 which comprises the use of a fluorine-containing pyrimidyl compound of the formula (4), in which each of $X_5$ and $V_5$ represents methyl, T represents chlorine and $An^\ominus$ represents a chloride ion and the trimethylammonium group is in the meta-position to the —NH— group.

11. A process according to claim 1 wherein the treatment of the cellulose material with the fluorine-containing cationic compound is carried out before or after the dyeing.

12. A process according to claim 11 wherein the treatment of the cellulose material is carried out after the dyeing.

13. A process according to claim 11 wherein the pre- or aftertreatment of the cellulose material is carried out by an exhaustion process.

14. A process according to claim 11 wherein the pre- or aftertreatment of the cellulose material is carried out by a cold pad-batch process.

* * * * *